(12) United States Patent
Zheng

(10) Patent No.: US 9,517,322 B2
(45) Date of Patent: Dec. 13, 2016

(54) FLOWMETER

(71) Applicant: Beijing Aeonmed Co., Ltd., Beijing (CN)

(72) Inventor: Dianhui Zheng, Beijing (CN)

(73) Assignee: BEIJING AEONMED CO., LTD, Beijing (CN)

( * ) Notice: Subject to any disclaimer, the term of this patent is extended or adjusted under 35 U.S.C. 154(b) by 536 days.

(21) Appl. No.: 14/002,358

(22) PCT Filed: Dec. 25, 2012

(86) PCT No.: PCT/CN2012/087388
§ 371 (c)(1),
(2) Date: Aug. 29, 2013

(87) PCT Pub. No.: WO2013/097695
PCT Pub. Date: Jul. 4, 2013

(65) Prior Publication Data
US 2014/0283830 A1     Sep. 25, 2014

(30) Foreign Application Priority Data

Dec. 30, 2011   (CN) .......................... 2011 1 0457021

(51) Int. Cl.
*A61M 16/10* (2006.01)
*A61M 16/20* (2006.01)
(Continued)

(52) U.S. Cl.
CPC .......... *A61M 16/201* (2014.02); *A61M 16/01* (2013.01); *A61M 16/122* (2014.02); *A61M 16/20* (2013.01);
(Continued)

(58) Field of Classification Search
CPC ........... G01F 1/26; G01F 1/22; A61M 16/209; A61M 16/20; A61M 2205/3334; A61M 16/201; A61M 16/122; A61M 15/01; A61M 16/1005; A61M 2016/003
(Continued)

(56) References Cited

U.S. PATENT DOCUMENTS 1,430,097 A * 9/1922 Mills ................... B60C 23/0496
137/224
2,073,372 A * 3/1937 Heidbrink ............. A61M 16/10
128/205.23
(Continued)

FOREIGN PATENT DOCUMENTS

CN           2816757 Y      9/2006
CN         102269604 A     12/2011
(Continued)

OTHER PUBLICATIONS

International Search Report issued in International Application No. PCT/CN2012/087388 dated Mar. 14, 2013.

*Primary Examiner* — Marina Tietjen
*Assistant Examiner* — Umashankar Venkatesan
(74) *Attorney, Agent, or Firm* — Venable LLP; Henry J. Daley; Tamatane J. Aga

(57) ABSTRACT

A flowmeter comprises a lower valve body (1), a throttle assembly, a flow tube assembly, an upper valve body (2), and a pressure fluctuation suppression assembly. An air inlet, an air outlet and an air flow channel connecting the air inlet and the air outlet are arranged in the lower valve body (1); a throttle assembly for adjusting the degree of opening of the air flow channel in the lower valve body (1) is further disposed on the lower valve body (1). The flow tube assembly comprises a flow tube (3), an upper base (4), a lower base (5), and a float (6); a vent hole is provided on each of axial centers of the upper base (4) and the lower base (5); the lower base (5) is arranged at the air outlet of the lower valve body (1); a vertical air flow passage and a (Continued)

horizontal air flow passage are arranged in the upper valve body (2); the upper base (4) is arranged at an air inlet of the vertical air flow passage in the upper valve body (2); the flow tube (3) is disposed between the upper base (4) and the lower base (5) through two ends thereof that are respectively sleeved on protruding portions of the upper base (4) and the lower base (5); the float (6) is disposed in the flow tube (3). The pressure fluctuation suppression assembly comprises a sealing gasket (7), and the sealing gasket (7) is disposed at an air outlet of the vertical air flow passage.

6 Claims, 3 Drawing Sheets

(51) Int. Cl.
    *A61M 16/01*     (2006.01)
    *G01F 1/22*     (2006.01)
    *A61M 16/12*     (2006.01)
    *G01F 1/26*     (2006.01)
    *A61M 16/00*     (2006.01)

(52) U.S. Cl.
    CPC .............. *A61M 16/209* (2014.02); *G01F 1/22* (2013.01); *G01F 1/26* (2013.01); *A61M 16/1005* (2014.02); *A61M 2016/003* (2013.01); *A61M 2205/3334* (2013.01)

(58) Field of Classification Search
    USPC ... 137/494, 497, 500, 503, 504; 128/204.28, 128/205.23, 205.24, 204.26
    See application file for complete search history.

(56) References Cited

U.S. PATENT DOCUMENTS

| | | | | |
|---|---|---|---|---|
| 2,416,881 | A | * | 3/1947 | Osborn ................. G05D 16/10 137/115.2 |
| 3,586,045 | A | * | 6/1971 | Zimmer ................ A61M 16/10 137/505.18 |
| 5,265,594 | A | | 11/1993 | Olsson et al. |
| 2014/0332097 | A1 | * | 11/2014 | Twitchett ............... G05D 7/012 137/504 |

FOREIGN PATENT DOCUMENTS

| | | |
|---|---|---|
| CN | 202453013 U | 9/2012 |
| FR | 2800285 A1 | 5/2001 |
| JP | 2003247695 A | 9/2003 |
| JP | 2004223257 A | 8/2004 |

\* cited by examiner

FLOWMETER

FIELD OF THE INVENTION

The present invention relates to a flowmeter, and more particularly, to a flowmeter for an anesthesia machine.

BACKGROUND OF THE INVENTION

The flowmeter, as an essential part of the anesthesia machine, may be adjusted by a doctor to provide for a suitable flow of oxygen to a patient. The existing flowmeter for the anesthesia machine has the following problems that: (1) the flowmeter float beats during the normal operation of the bellows of the anesthesia machine; (2) the air within the flowmeter cannot be discharged effectively in the case of excessive air resistance at the flowmeter outlet; and (3) its structure is complex and its manufacture cost is high.

SUMMARY OF THE INVENTION

The aim of the invention is to provide a flowmeter, in order to solve the problems of the existing flowmeter used for an anesthesia machine, including a complex structure and a high manufacture cost, beating of the float of the flowmeter during the normal working of the bellows, and the ineffective discharge of the air within the flowmeter in the case of excessive air resistance at the flowmeter outlet.

The aim of the invention is realized through the following technical schemes.

A flowmeter includes a lower valve body, a throttle valve assembly, a flow tube assembly, an upper valve body and a pressure fluctuation suppressing assembly, wherein the lower valve body is provided with an air inlet, an air outlet and an airflow passage in communication with the air inlet and the air outlet; the lower valve body is also provided with a throttle valve assembly used for adjusting the open degree of the airflow passage in the lower valve body; the flow tube assembly includes a flow tube, an upper base, a lower base and a float, wherein a ventilation hole is provided axially at the center of each of the upper base and the lower base, the lower base is arranged at the air outlet of the lower valve body, a vertical airflow passage and a horizontal airflow passage are provided within the upper valve body, the upper base is arranged at an air inlet of the vertical airflow passage in the upper valve body, the flow tube is arranged between the upper base and the lower base in such a way that protruding ends of the upper base and the lower base are inserted into both ends of the flow tube 3, respectively, the float is arranged within the flow tube, and the pressure fluctuation suppressing assembly includes a sealing gasket which is arranged at an air outlet of the vertical airflow passage.

Preferably, the flowmeter further includes a safety valve arranged on the valve body, and an air inlet of the safety valve is in communication with the horizontal airflow passage.

Preferably, the safety valve assembly includes a safety valve body, a safety valve stem, a sealing ring, a spring, a stop block and a nut; a through hole is provided axially at the center of the safety valve body; a stop step, on end face of which is a conical surface, is provided within the through hole along the central axis of the through hole, the safety valve stem includes a columnar rod and a conical valve head, one end of the columnar rod is connected with the smaller end of the conical valve head, and the other end is provided with threads; the conical surface of the conical valve head is provided with an annular groove, into which a sealing ring is arranged, the safety valve stem is arranged in the safety valve body, the columnar rod of the valve stem extends through the spring, which is arranged between the stop block and the stop step through the stop block and the nut; the conical valve head is in sealed contact with the conical surface of the stop step through the sealing ring arranged in the annular groove of the valve head, and the gap between the conical surface of the conical valve head and the conical surface of the stop step is in communication with the horizontal airflow passage.

Preferably, the throttle valve assembly includes a throttle valve body, a throttle ring, a throttle valve stem and a knob, the throttle valve body contains a through hole along its central axis, the throttle ring is placed inside the through hole at one end of the throttle valve body 13, an air outlet is radially arranged in a portion of the throttle valve body that follows the throttle ring, the end with the throttle ring of the throttle valve body is screwed into a hole particularly provided in the lower valve body, the air intake at the center of the throttle ring is in communication with an air inlet of the lower valve body, the air outlet of the throttle valve body is in communication with the air outlet on the lower valve body, one end of the throttle valve stem is a needle-shaped throttle end which is screwed into the through hole provided axially at the center of the throttle valve body and cooperates with the air intake at the center of the throttle ring to realize a throttle function, and the other end of the throttle valve stem is fixedly connected with the knob.

Preferably, the throttle valve assembly further includes a locking knob for limiting a length by which the throttle valve stem extrudes from the throttle valve body, and the throttle valve stem extends through the locking knob, which is further screwed onto an end of the throttle valve body that is opposite to the end with the throttle ring.

Preferably, the throttle valve assembly further includes a locking ring which is fixed on the throttle valve stem between the locking knob and the knob and used for limiting a length by which the throttle valve stem is retracted into the throttle valve body.

Preferably, the flowmeter further includes a backlight plate arranged at a rear side of the flow tube, upper and lower ends of the backlight plate are respectively arranged within a groove particularly provided on the lower valve body and a step particularly provided on the upper valve body, and the upper end is fixed by a pressing plate which is fixed on the upper valve body by a screw.

Preferably, the sealing gasket has a star shape.

The working principle of the invention is described as follows. The float of flowmeter is prevented from beating during the normal working of the bellows of the anesthesia machine through a pressure fluctuation suppressing assembly within the flowmeter, such as a sealing gasket which functions to share and undertake air pressure; and the air within the flowmeter can be discharged effectively and the air pressure can be reduced automatically through a safety valve provided on the flowmeter when the air resistance at the flowmeter outlet is excessive.

The invention is advantageous in that: (1) the flowmeter float is prevent from beating when the anesthesia machine bellows works normally; (2) the air within the flowmeter can be discharged effectively and the pressure in the flowmeter can be reduced automatically in the case of excessive air resistance at the flowmeter outlet; and (3) the flowmeter has a simple structure and a low manufacture cost.

BRIEF DESCRIPTION OF THE DRAWINGS

The present invention will be further illustrated in detail with reference to the accompanying drawings and embodiments.

Figure 1:
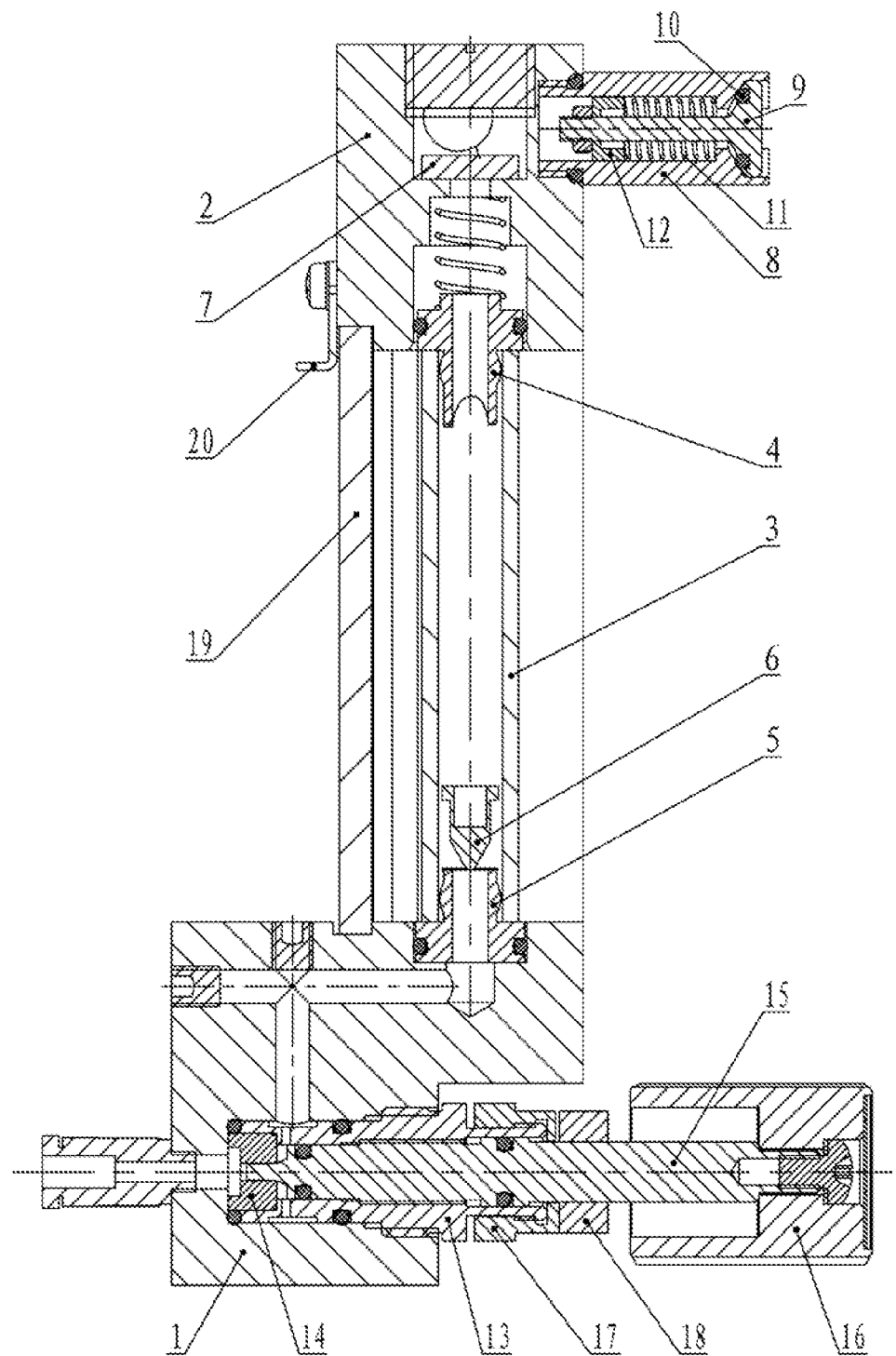
FIG. 1 is a schematic sectional view of the flowmeter of an embodiment of the invention.

| List of reference numerals: | | |
|---|---|---|
| 1: Lower valve body; | 2: Upper valve body; | 3: Flow tube; |
| 4: Upper base; | 5: Lower base; | 6: Float; |
| 7: Sealing gasket; | 8: Safety valve body; | 9: Safety valve stem; |
| 10: Sealing ring; | 11: Spring; | 12: Stop block; |
| 13: Throttle valve body; | 14: Throttle ring; | 15: Throttle valve stem; |
| 16: Knob; | 17: Locking knob; | 18: Locking ring; |
| 19: Backlight plate; | 20: Pressing plate. | |

DETAILED DESCRIPTION OF THE EMBODIMENTS

Figure 2:
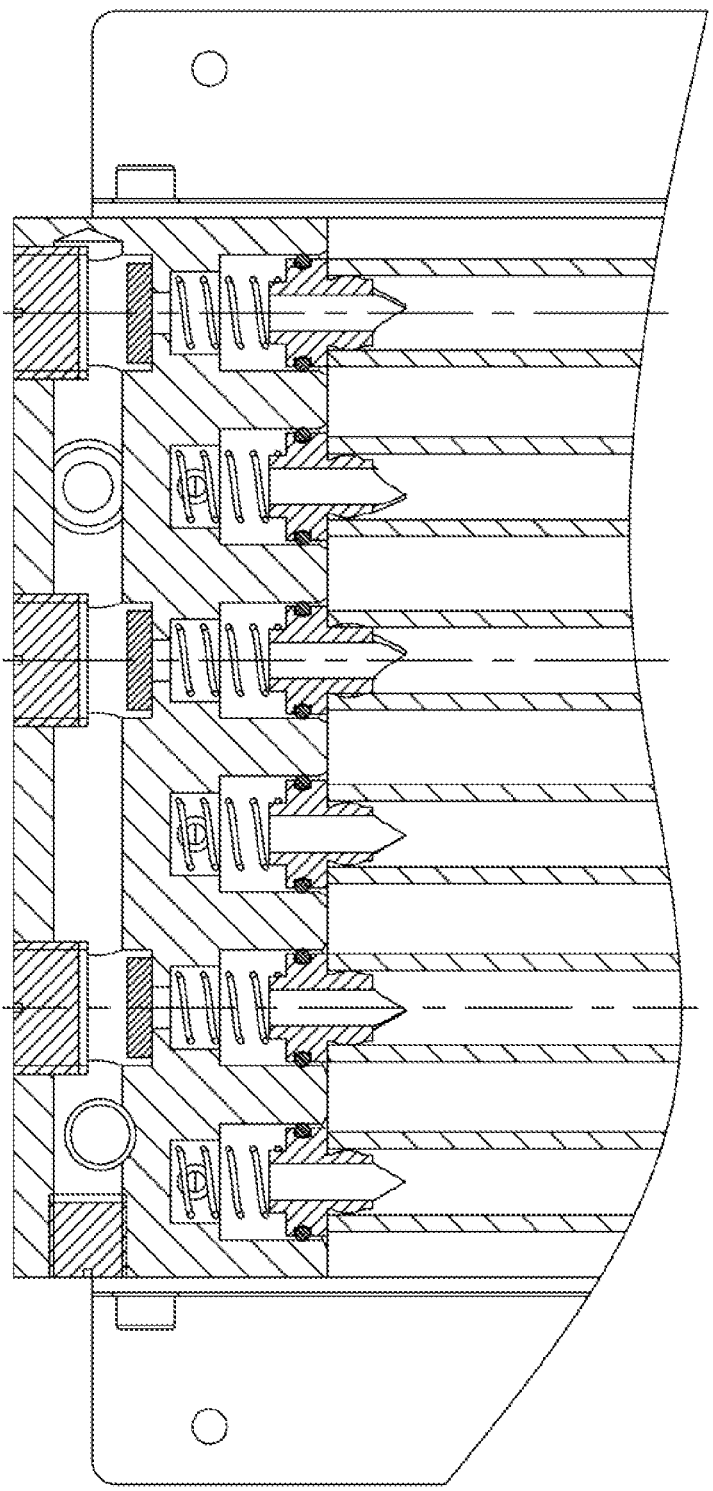
FIG. 2 is the schematic sectional view of the upper valve body of the flowmeter shown in FIG. 1.
Figure 3:
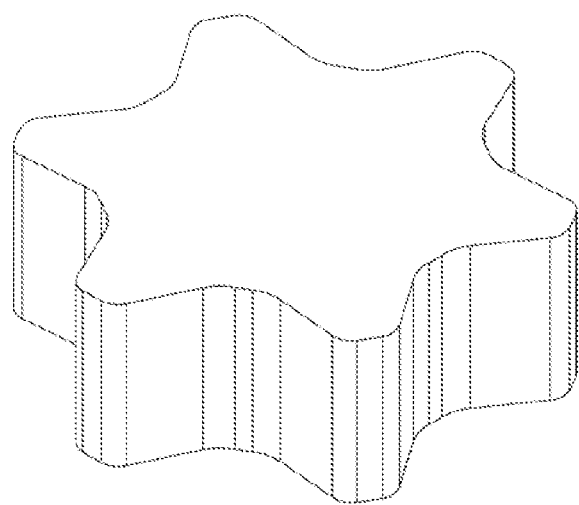
FIG. 3 is a schematic perspective view of the sealing gasket of the flowmeter shown in FIG. 1.

As shown in FIGS. 1-3, a flowmeter of an embodiment includes a lower valve body 1, a throttle valve assembly, a flow tube assembly, an upper valve body 2 and a pressure fluctuation suppressing assembly. The lower valve body 1 contains an air inlet, an air outlet, and an airflow passage in communication with the air inlet and the air outlet, and is also provided with a throttle valve assembly used for adjusting the open degree of the airflow passage in the lower valve body 1. The flow tube assembly includes a flow tube 3, an upper base 4, a lower base 5 and a float 6, where a ventilation hole is provided axially at the center of each of the upper base 4 and the lower base 5, and the lower base 5 is arranged at the air outlet of the lower valve body 1. A vertical airflow passage and a horizontal airflow passage are provided within the upper valve body 2, the upper base 4 is arranged at an air inlet of the vertical airflow passage in the upper valve body, the flow tube 3 is arranged between the upper base 4 and the lower base 5 in such a way that protruding ends of the upper base 4 and the lower base 5 are inserted into both ends of the flow tube 3, respectively, and the float 6 is arranged within the flow tube 3. The pressure fluctuation suppressing assembly includes a sealing gasket 7 which is arranged at an air outlet of the vertical airflow passage.

The flowmeter further includes a safety valve arranged on the valve body 2, and an air inlet of the safety valve is in communication with the horizontal airflow passage.

The safety valve assembly includes a safety valve body 8, a safety valve stem 9, a sealing ring 10, a spring 11, a stop block 12 and a nut. A through hole is provided axially at the center of the safety valve body 8, and a stop step, one end face of which is a conical surface, is provided within the through hole along the central axis of the through hole. The safety valve stem 9 includes a columnar rod and a conical valve head, one end of the columnar rod is connected with the smaller end of the conical valve head, and the other end is provided with threads. The conical surface of the conical valve head is provided with an annular groove, into which a sealing ring 10 is arranged. The safety valve stem 9 is arranged in the safety valve body 8, and the columnar rod of the safety valve stem 9 extends through the spring 11, which is arranged between the stop block 12 and the stop step through the block 12 and the nut. The conical valve head is in sealed contact with the conical surface of the stop step through the sealing ring 10 arranged in the annular groove of the valve head, and the gap between the conical surface of the conical valve head and the conical surface of the stop step is in communication with the horizontal airflow passage.

The throttle valve assembly includes a throttle valve body 13, a throttle ring 14, a throttle valve stem 15 and a knob 16. The throttle valve body 13 contains a through hole along its central axis, the throttle ring 14 is placed inside the through hole at one end of the throttle valve body 13, an air outlet is radially arranged in a portion of the throttle valve body 13 that follows the throttle ring 14, the air intake at the center of the throttle ring 14 is in communication with an air inlet of the lower valve body 1, and the air outlet of the throttle valve body 13 is in communication with the air outlet of the lower valve body 1. One end of the throttle valve stem 15 is a needle-shaped throttle end which is screwed into the through hole provided axially at the center of the throttle valve body 13 and cooperates with the air intake at the center of the throttle ring 14 to realize a throttle function, and the other end of the throttle valve stem 15 is fixedly connected with the knob 16.

The throttle valve assembly also includes a locking knob 17 for limiting a length by which the throttle valve stem 15 extrudes from the throttle valve body 13, and the throttle valve stem 15 extends through the locking knob 17, which is further screwed onto an end of the throttle valve body 13 that is opposite to the end with the throttle ring.

The throttle valve assembly also includes a locking ring 18, which is fixed on the throttle valve stem 15 between the locking knob 17 and the knob 16 and used for limiting a length by which the throttle valve stem 15 is retracted into the throttle valve body 13.

The flowmeter also includes a backlight plate 19 arranged at the rear side of the flow tube 3, upper and lower ends of the backlight plate 19 are respectively arranged within a groove particularly provided on the lower valve body 1 and a step particularly provided on the upper valve body 2, and the upper end is fixed by a pressing plate 20 which is fixed on the upper valve body 2 by a screw.

The sealing gasket 7 has a star shape, and peripheral protrusions of the star shape are placed in the corresponding recessions of the upper valve body 2 for the purpose of position limiting.

The working process of the flowmeter in the embodiment is described as follows. Air may flows into the airflow passage within the lower valve body 1 from the air inlet of the lower valve body, and then arrives at the throttle ring 14 of the throttle valve assembly. At this point, the air intake at the center of the throttling ring 14 may be opened by adjusting the knob 16, and the air arrives at the lower base 5 through the air intake at the center of the throttling ring 14, the air outlet radially arranged in a portion of the throttle valve body 13 that follows the throttle ring 14, and the airflow passage within the lower valve body 1, and enters into the ventilation hole axially provided at the center of the lower base 5. In this case, the air pushes the float 6 upwards to open the ventilation hole provided axially at the center of the lower base 5, then flows into the flow tube 3 through the ventilation hole provided axially at the center of the lower base 5, and further flows to the upper base 4 through the gap between the float 6 and the flow tube 3. Subsequently, the air flows through the ventilation hole provided axially at the center of the lower base 4, enters into the vertical airflow passage provided within the upper valve body 2, and pushes away the sealing gasket 7 provided at the air outlet of the vertical airflow passage, then flows into the horizontal airflow passage provided within the upper valve body 2, and finally flows into the following equipment connected with the flowmeter from the air outlet of the upper valve body 2.

The pressure in the horizontal airflow passage of the upper valve body 2 of the flowmeter increases when the air resistance of the following equipment connected with the flowmeter is increased. The air pushes and separates the safety valve stem 9 from the safety valve body 8 when the pressure in the horizontal airflow passage reaches the preset value, so that partial air is discharged from the air outlet of the safety valve body 8, the pressure within the horizontal flow passage of the upper valve body 2 drops accordingly, and the safety valve stem 9 returns to its initial position under the action of the spring 11 and again is in sealing contact with the safety valve body 8 when the pressure in the horizontal airflow passage is lower than the preset value.

When the flowmeter of the embodiment is used in an anesthesia machine and the bellows of the anesthesia machine works normally, cyclical pressure fluctuation exists within the horizontal flow passage and the vertical flow passage of the upper valve body 2 due to the cyclical resistance fluctuation subsequent to the flowmeter, in this case, the sealing gasket 7 functions to share and undertake the pressure during the pressure fluctuation, so that the impact on the float 6 by the pressure fluctuation is decreased, thereby the float 6 is prevent from beating when the bellows works normally.

The invention is advantageous in that: (1) the flowmeter float is prevent from beating when the anesthesia machine bellows works normally; (2) the air within the flowmeter can be discharged effectively and the pressure in the flowmeter can be reduced automatically in the case of excessive air resistance at the flowmeter outlet; and (3) the flowmeter has a simple structure and a low manufacture cost.

The invention claimed is:

1. A flowmeter, comprising a lower valve body, a throttle valve assembly, a flow tube assembly, an upper valve body and a pressure fluctuation suppressing assembly, wherein the lower valve body is provided with an air inlet, an air outlet and an airflow passage in communication with the air inlet and the air outlet; the lower valve body is also provided with a throttle valve assembly used for adjusting the open degree of the airflow passage in the lower valve body;

the flow tube assembly includes a flow tube, an upper base, a lower base and a float, wherein a ventilation hole is provided axially at the center of each of the upper base and the lower base, the lower base is arranged at the air outlet of the lower valve body, a vertical airflow passage and a horizontal airflow passage are provided within the upper valve body, the upper base is arranged at an air inlet of the vertical airflow passage in the upper valve body, the flow tube is arranged between the upper base and the lower base in such a way that protruding ends of the upper base and the lower base are inserted into both ends of the flow tube, respectively, the float is arranged within the flow tube, and the pressure fluctuation suppressing assembly comprises a sealing gasket which is arranged at an air outlet of the vertical airflow passage:

a safety valve arranged on the valve body, and an air inlet of the safety valve is in communication with the horizontal airflow passage;

wherein the safety valve comprises a safety valve body, a safety valve stem, a sealing ring, a spring, a stop block and a nut: a through hole is provided axially at the center of the safety valve body a stop step, on end face of which is a conical surface, is provided within the through hole along the central axis of the through hole, the safety valve stem comprises a columnar rod and a conical valve head, one end of the columnar rod is connected with the smaller end of the conical valve head, and the other end is provided with threads: the conical surface of the conical valve head is provided with an annular groove, into which a sealing ring is arranged, the safety valve stem is arranged in the safety valve body, the columnar rod of the valve stem extends through the spring, which is arranged between the stop block and the stop step through the stop block and the nut the conical valve head is in sealed contact with the conical surface of the stop step through the sealing ring arranged in the annular groove of the valve head, and the gap between the conical surface of the conical valve head and the conical surface of the stop step is in communication with the horizontal airflow passage.

2. The flowmeter of claim 1, wherein the throttle valve assembly comprises a throttle valve body, a throttle ring, a throttle valve stem and a knob, the throttle valve body contains a through hole along its central axis, the throttle ring is placed inside the through hole at one end of the throttle valve body, an air outlet is radially arranged in a portion of the throttle valve body that follows the throttle ring, the end with the throttle ring of the throttle valve body is screwed into a hole particularly provided in the lower valve body, the air intake at the center of the throttle ring is in communication with an air inlet of the lower valve body, the air outlet of the throttle valve body is in communication with the air outlet on the lower valve body, one end of the throttle valve stem is a needle-shaped throttle end which is screwed into the through hole provided axially at the center of the throttle valve body and cooperates with the air intake at the center of the throttle ring to realize a throttle function, and the other end of the throttle valve stem is fixedly connected with the knob.

3. The flowmeter of claim 2, wherein the throttle valve assembly further comprises a locking knob for limiting a length by which the throttle valve stem extrudes from the throttle valve body, and the throttle valve stem extends through the locking knob, which is further screwed onto an end of the throttle valve body that is opposite to the end with the throttle ring.

4. The flowmeter of claim 3, wherein the throttle valve assembly further comprises a locking ring which is fixed on the throttle valve stem between the locking knob and the knob and used for limiting a length by which the throttle valve stem is retracted into the throttle valve body.

5. The flowmeter of claim 1, further comprising a backlight plate arranged at a rear side of the flow tube, upper and lower ends of the backlight plate are respectively arranged within a groove particularly provided on the lower valve body and a step particularly provided on the upper valve body, and the upper end is fixed by a pressing plate which is fixed on the upper valve body by a screw.

6. The flowmeter of claim 1, wherein the sealing gasket has a star shape.

* * * * *